United States Patent [19]

Nishiyama et al.

[11] 4,230,642

[45] Oct. 28, 1980

[54] PROCESS FOR PRODUCING 3,5-DICHLORO-α-METHYLSTYRENE

[75] Inventors: Ryuzo Nishiyama, Takatsuki; Kanichi Fujikawa, Kusatsu; Yasuhiro Tsujii, Kusatsu; Itaru Shigehara, Kusatsu, all of Japan

[73] Assignee: Ishihara Sangyo Kaisha Limited, Osaka, Japan

[21] Appl. No.: 9,178

[22] Filed: Feb. 2, 1979

[30] Foreign Application Priority Data

Feb. 27, 1978 [JP] Japan .................................. 53-21812

[51] Int. Cl.$^2$ ............................................. C07G 25/00
[52] U.S. Cl. .................................................. 570/193
[58] Field of Search .................................... 260/650 R

[56] References Cited

U.S. PATENT DOCUMENTS

| 2,192,613 | 3/1940 | Livak et al. ....................... 260/650 R |
| 2,725,405 | 11/1955 | Britton et al. ..................... 260/650 R |
| 2,996,554 | 8/1961 | Olah et al. ........................ 260/650 R X |
| 3,042,664 | 7/1962 | Price ............................... 260/650 R X |
| 3,167,714 | 10/1973 | Kominami et al. .............. 260/650 R |
| 3,911,034 | 10/1975 | Sato et al. ........................ 260/650 R |

FOREIGN PATENT DOCUMENTS

| 687266 | 4/1948 | United Kingdom ................ 260/650 R |
| 687267 | 4/1948 | United Kingdom ................ 260/650 R |
| 652618 | 4/1951 | United Kingdom ................ 260/650 R |

OTHER PUBLICATIONS

Stempel, JACS 73 455-456 (1951) from C.A. 46 2001e (1952).
Chemical Abstracts 52 11917a-c (1958).
Chemical Abstracts 47 10899b (1953).
Chemical Abstracts 42 3339i (1948).

*Primary Examiner*—Helen M. S. Sneed
*Attorney, Agent, or Firm*—Oblon, Fisher, Spivak, McClelland & Maier

[57] ABSTRACT

1-Bromo-3,5-dichlorobenzene is reacted with magnesium in a solvent and acetone is added to react it with the reaction product and a mineral acid is added to hydrolyze the resulting α-(3,5-dichlorophenyl) isopropoxymagnesium bromide and then, the product is dehydrated to obtain 3,5-dichloro-α-methylstyrene. 3,5-Dichloro-α-methylstyrene is useful intermediate for various agricultural chemicals, medicines and dyes and also useful monomer for rubbers, plastics and resins.

3 Claims, No Drawings

PROCESS FOR PRODUCING 3,5-DICHLORO-α-METHYLSTYRENE

BACKGROUND OF THE INVENTION

1. Field of the Invention

The present invention relates to a novel process for producing 3,5-dichloro-α-methylstyrene from 1-bromo-3,5-dichlorobenzene.

3,5-Dichloro-α-methylstyrene is useful intermediate for various agricultural chemicals, medicines and dyes and also useful monomer for rubbers, plastics and resins.

2. Description of the Prior Arts

An industrial process for producing 3,5-dichloro-α-methylstyrene has not been developed.

The inventors have studied on various processes for finding an industrially advantageous process for producing 3,5-dichloro-α-methylstyrene. As the results, the inventors have found that bromine atom in 1-bromo-3,5-dichlorobenzene which could be economically produced in a mass production, has significantly higher reactivity to magnesium than that of chlorine atom and accordingly, the object compound of 3,5-dichloro-α-methylstyrene can be effectively produced in an industrial scale from 1-bromo-3,5-dichlorobenzene obtained in a mass production.

It has been known that 3,5-dichloro-α-methylstyrene can be produced by reacting thionyl chloride with 3,5-dichlorobenzoic acid to obtain 3,5-dichlorobenzoyl chloride and then reacting methanol with 3,5-dichlorobenzoyl chloride to obtain methyl-3,5-dichlorobenzoate and reacting methylmagnesium chloride with methyl-3,5-dichlorobenzoate in ether and then, hydrolyzing the product with a diluted hydrochloric acid and dehydrating the product over sodium bisulfate, in for example, Journal of the American Chemical Society 73 January 1951, page 455–456. However, this process is not advantageous as an industrial process because many reaction steps are needed for producing methyl3,5-dichlorobenzoate and a complicated reaction step is included in these steps for producing the starting material and the hydrolysis and the dehydration should be separately carried out.

SUMMARY OF THE INVENTION

It is an object of the present invention to provide a process for producing 3,5-dichloro-α-methylstyrene having high purity in an industrially advantageous process.

The other objects of the present invention will be apparent from the following description.

The foregoing objects of the present invention have been attained by providing a process for producing 3,5-dichloro-α-methylstyrene which comprises (A) reacting magnesium with 1-bromo-3,5-dichlorobenzene in a solvent; (B) reacting acetone with the resulting reaction product and (C) hydrolyzing the resulting α-(3,5-dichlorophenyl) isopropoxy magnesium bromide with a mineral acid and dehydrating the product.

DETAILED DESCRIPTION OF THE PREFERRED EMBODIMENTS

The advantages of the present invention are as follows.

(1) 3,5-Dichloro-α-methylstyrene having a purity of higher than 90% is usually obtained in high yield such as higher than 70% in accordance with the process of the present invention.

(2) The starting material, 1-bromo-3,5-dichlorobenzene has not been economically produced but the inventors have found an economically advantageous process for producing 1-bromo-3,5-dichlorobenzene in mass production which is disclosed in DOP (West German Unexamined Publication) No. 2,737,797, whereby 3,5-dichloro-α-methylstyrene can be produced in an economically advantageous process.

(3) When a hydrolysis and a dehydration is carried out in the presence of sulfuric acid or phosphoric acid in the step (C) of the process of the present invention, the steps (A) to (C) of the process of the present invention can be carried out without separating a reaction product from the reaction system to be significantly advantageous.

Detail of the embodiments of the process of the present invention will be illustrated.

In the process of the present invention, 3,5-dichlorophenylmagnesium bromide is obtained by reacting 1-bromo-3,5-dichlorobenzene with magnesium in the presence of a solvent.

Suitable solvents include ethers such as diethyl ether and tetrahydrofuran. From the industrial viewpoint, it is preferable to use tetrahydrofuran.

In the reaction, bromine atom in 1-bromo-3,5-dichlorbenzene has significantly higher reactivity to magnesium than that of the chlorine atom in it. Therefore, 3,5-dichlorophenylmagnesium bromide is obtained by reacting bromine atom of 1-bromo-3,5-dichlorobenzene predominantly with magnesium.

It is preferable to use magnesium having higher purity in equal mole or slightly excess such as 1 to 1.5 mole preferably 1 to 1.2 mole per 1 mole of 1-bromo-3,5-dichlorobenzene.

A reaction temperature is usually in a range of 10° to 70° C. preferably 20° to 50° C. and a reaction time is usually in a range of 0.1 to 5 hours preferably 0.5 to 2 hours.

3,5-Dichlorophenylmagnesium bromide obtained in the former step and dissolved in a solvent is usually reacted with acetone without separating from the reaction system. In general, acetone is added to the reaction mixture containing 3,5-dichlorophenylmagnesium bromide to react them at 0° to 70° C. preferably 20° to 50° C. for 0.1 to 5 hours preferably 0.5 to 2 hours to obtain α-(dichlorophenyl) isopropoxymagnesium bromide.

In an industrial process, it is preferable to add stoichometrical amount or slightly excess of acetone to 3,5-dichlorophenylmagnesium bromide.

The resulting solution of α-(3,5-dichlorophenyl) isopropoxymagnesium bromide is used in the next steps of the hydrolysis and the dehydration with a mineral acid.

Suitable mineral acids include sulfuric acid, phosphoric acid, and hydrochloric acid.

An amount of the mineral acid is in a range of 1 to 5 equimole to α-(3,5-dichlorophenyl) isopropoxymagnesium bromide.

When hydrochloric acid is used as the mineral acid, the hydrolyzed product is separated from the reaction system and the product is dehydrated with $P_2O_5$, sulfuric acid or phosphoric acid. However, when the hydrolysis is carried out in the presence of sulfuric acid or phosphoric acid, the hydrolysis and the dehydration can be carried out without any separation under a simple control of reaction conditions, whereby this feature is advantageous in an industrial process.

For example, when the solution containing α-(3,5-dichlorophenyl) isopropoxymagnesium bromide is added to an aqueous solution of 20 to 80% sulfuric acid or phosphoric acid at 0° to 100° C., preferably 20° to 70° C. to perform the hydrolysis immediately and accordingly, the mixture is heated at 80° to 120° C. preferably 100° to 115° C. for 1 to 3 hours to dehydrate the product.

The aqueous solution of sulfuric acid or phosphoric acid is added in a range of 1 to 5 equimole as the acid to α-(3,5-dichlorophenyl) isopropoxymagnesium bromide.

The solvent is distilled off during the dehydration at the elevated temperature, and accordingly, the solvent is recovered and recycled.

In the preferred embodiment for recovering the solvent, the hydrolysis is carried out in the presence of a diluted hydrochloric acid needed for the hydrolysis, and then, the solvent is recovered and then, the dehydration is carrid out by adding sulfuric acid.

The reaction mixture is usually separated by a phase separation into a water phase containing an inorganic salt and an oil phase. The oil phase is washed with an aqueous solution of a base and it is post-treated by a steam distillation, a phase separation and, if desired, a distillation in order to obtain 3,5-dichloro-α-methylstyrene having a purity of higher than 95%.

The present invention will be illustrated by certain examples and references which are provided for purposes of illustration only and are not intended to be limiting the present invention.

EXAMPLE 1

16.2 Grams of powdery magnesium (purity 99.5%) was dispersed in 66.2 ml of tetrahydrofuran. A solution obtained by dissolving 150.6 g of 1-bromo-3,5-dichlorobenzene in 132.4 ml of tetrahydrofuran was added dropwise to the dispersion heated at 30° C. and after the addition, the mixture was stirred at the same temperature for 2 hours to react them whereby 3,5-dichlorophenylmagnesium bromide was produced. Then, 38.7 g of acetone was added dropwise to the reaction mixture and after the addition, the mixture was stirred at 40° C. for 1 hour to react them whereby α-(3,5-dichlorophenyl) isopropoxymagnesium bromide was produced. The reaction mixture was poured into an aqueous solution of sulfuric acid prepared by using 180 g of sulfuric acid and 200 ml of water and a hydrolysis was carried out at lower than 70° C. and then, the solvent was distilled off by elevating the temperature and then, a dehydration was carried out at 110° C. for 2 hours. A phase separation of the reaction mixture was carried out and 26.8 g of 40% aqueous solution of sodium hydroxide and 30 ml of water were added to the oil phase and a steam distillation was carried out at 100° to 110° C. for 4 hours.

The distilled product was further distilled under a reduced pressure to obtain 100 g of the object compound having a boiling point 155° C./100 mmHg which had a purity of 96% at an yield of 80% to 1-bromo-3,5-dichlorobenzene.

EXAMPLE 2

27 Grams of powdery magnesium (purity 99.5%) was dispersed in 200 ml of diethyl ether. A solution obtained by dissolving 226 g of 1-bromo-3,5-dichlorobenzene in 800 ml of diethyl ether was added dropwise to the dispersion heated at about 40° C., and after the addition, the mixture was stirred at the same temperature for 2 hours to react them whereby 3,5-dichlorophenylmagnesium bromide was produced. Then, 60 g of acetone was added dropwise to the reaction mixture and after the addition, the mixture was stirred at 30° to 40° C. for 1 hour to react them whereby α-(3,5-dichlorophenyl) isopropoxymagnesium bromide was produced. The reaction mixture was poured into 600 g of 45% aqueous solution of sulfuric acid and a hydrolysis was carried out at lower than 50° C. and then, the solvent was distilled off by elevating the temperature and then, a dehydration was carried out at 110° C. for 2 hours. A phase separation was carried out and the oil phase was washed with water, an aqueous solution of a base and water in the order and then a phase separation was carried out. The product was distilled under a reduced pressure to obtain 152 g of the object compound which had a purity of 97% at an yield of 81% to 1-bromo-3,5-dichlorobenzene.

What is claimed is:

1. A process for producing 3,5-dichloro-α-methylstyrene which comprises a step (a) of reacting magnesium with 1-bromo-3,5-dichlorobenzene in the presence of an ether solvent at a reaction temperature in a range of 10° to 70° C., wherein the amount of magnesium is in a range of 1 to 1.5 mole per mole of 1-bromo-3,5-dichlorobenzene; a step (b) of adding acetone to the reaction mixture at a temperature in the range of 0° to 70° C.; and a step (c) of adding a mineral acid to the reaction mixture to hydrolyze the resulting α-(3,5-dichlorophenyl) isopropoxymagnesium bromide at a temperature in a range of 0° to 100° C.; and then dehydrating the product at a temperature in a range of 80° to 120° C.

2. A process according to claim 1 wherein the mineral acid is sulfuric acid or phosphoric acid.

3. A process according to claim 1 wherein an amount of the mineral acid is in a range of 1 to 5 equimoles to α-(3,5-dichlorophenyl) isopropoxymagnesium bromide.

* * * * *